(12) United States Patent
Nishinaka et al.

(10) Patent No.: US 7,328,474 B2
(45) Date of Patent: Feb. 12, 2008

(54) ELECTRIC TOOTHBRUSH WITH LINEAR OSCILLATOR

(75) Inventors: Takahiro Nishinaka, Omihachiman (JP); Hidekazu Yabuuchi, Hikone (JP); Hiroki Inoue, Hikone (JP); Tomio Yamada, Shiga (JP)

(73) Assignee: Matsushita Electric Works, Ltd., Kadoma-shi (JP)

( * ) Notice: Subject to any disclaimer, the term of this patent is extended or adjusted under 35 U.S.C. 154(b) by 498 days.

(21) Appl. No.: 10/340,632

(22) Filed: Jan. 13, 2003

(65) Prior Publication Data

US 2004/0010871 A1 Jan. 22, 2004

(30) Foreign Application Priority Data

Jan. 18, 2002 (JP) .............................. 2002-010823

(51) Int. Cl.
*A61C 17/34* (2006.01)
*H02K 33/00* (2006.01)

(52) U.S. Cl. ........................ 15/22.2; 15/22.1; 310/15; 310/17

(58) Field of Classification Search ................. 310/15, 310/17, 12, 81, 20, 23, 180, 181, 36; 15/22.1, 15/22.2

See application file for complete search history.

(56) References Cited

U.S. PATENT DOCUMENTS

| | | | |
|---|---|---|---|
| 2,648,787 A | | 8/1953 | Smithson, Jr. |
| 3,525,887 A | * | 8/1970 | Ewart, Jr. .................... 310/27 |
| 4,360,087 A | * | 11/1982 | Curwen ....................... 188/379 |
| 4,783,968 A | | 11/1988 | Higham et al. |
| 5,645,407 A | | 7/1997 | Kralick et al. |
| 6,958,553 B2 | * | 10/2005 | Ichii et al. .................... 310/15 |
| 2002/0195884 A1 | * | 12/2002 | Ichii et al. .................... 310/15 |

FOREIGN PATENT DOCUMENTS

FR 67 893 3/1958
JP 9-252843 9/1997

OTHER PUBLICATIONS

Patent of Abstracts of Japan, JP 9-252843, Sep. 30, 1997.

* cited by examiner

*Primary Examiner*—Gary K Graham
(74) *Attorney, Agent, or Firm*—Oblon, Spivak, McClelland, Maier & Neustadt, P.C.

(57) ABSTRACT

An electric toothbrush includes a drive part, a driver, a brush part and a vibration-absorber. The drive part includes a drive shaft provided to be lineally movable and a brush part detachably attached to one end of the drive shaft. The driver is configured to apply reciprocal force to the drive shaft to reciprocally lineally move the drive shaft. The vibration-absorber is connected to the drive shaft via a second spring to be lineally movable along the drive shaft. A weight ratio of a weight of the vibration-absorber to a weight of the drive part is at least 0.9 and at most 1.1.

27 Claims, 3 Drawing Sheets

ELECTRIC TOOTHBRUSH WITH LINEAR OSCILLATOR

CROSS-REFERENCE TO RELATED APPLICATIONS

The present application claims priority under 35 U.S.C. §119 to Japanese Patent Application No. 2002-010823, filed Jan. 18, 2002. The contents of this application are incorporated herein by reference in their entirety.

BACKGROUND OF THE INVENTION

1. Field of the Invention

The present invention relates to an electric toothbrush and a linear oscillator for the electric toothbrush.

2. Discussion of the Background

FIG. 3 shows an electric toothbrush of background art. Referring to FIG. 3, an electric toothbrush includes a linear oscillator 17. The linear oscillator 17 includes a shield case 16, a drive shaft 2 provided in the shield case 16 to be linearly movable. On the drive shaft 2, a vibration-absorber 12 is mounted in the axis direction with a distance from the plunger 3 so that the vibration-absorber 12 slides freely along the drive shaft 2. A brush part 1 is detachably attached to one shaft end (2a) of the drive shaft 2. A movable part 18 includes the drive shaft 2 and the plunger 3. A drive part includes the movable part 18 and the brush part 1.

In the electric toothbrush, in order to decrease the size of the linear oscillator 17, the space in which the vibration-absorber 12 vibrates is minimized. Thus, the weight of the vibration-absorber 12 is quite smaller compared to the weight of the drive part 19. In this linear oscillator, to give the specific oscillation or amplitude to the drive part 19, it has become necessary to make a larger magnetic circuit. As a result, the size of the linear oscillator 17 as a whole increases, and the number of parts also increases.

SUMMARY OF THE INVENTION

According to one aspect of the present invention, an electric toothbrush includes a drive part, a driver, a brush part and a vibration-absorber. The drive part includes a drive shaft provided to be lineally movable and a brush part detachably attached to one end of the drive shaft. The driver is configured to apply reciprocal force to the drive shaft to reciprocally lineally move the drive shaft. The vibration-absorber is connected to the drive shaft via a second spring to be lineally movable along the drive shaft. A weight ratio of a weight of the vibration-absorber to a weight of the drive part is at least 0.9 and at most 1.1.

According to another aspect of the present invention, a linear oscillator includes a movable part, a driver and a vibration-absorber. The movable part includes a drive shaft provided to be lineally movable. The driver is configured to apply reciprocal force to the drive shaft to reciprocally lineally move the drive shaft. The vibration-absorber is connected to the drive shaft via a second spring to be lineally movable along the drive shaft. A weight ratio of a weight of the vibration-absorber to a sum of a weight of the movable part and a weight of a brush part which is configured to be detachably attached to one end of the drive shaft is at least 0.9 and at most 1.1.

BRIEF DESCRIPTION OF THE DRAWINGS

A more complete appreciation of the invention and many of the attendant advantages thereof will become readily obtained as the same becomes better understood with reference to the following detailed description when considered in conjunction with the accompanying drawings, wherein.

DESCRIPTION OF THE EMBODIMENTS

Figure 1:
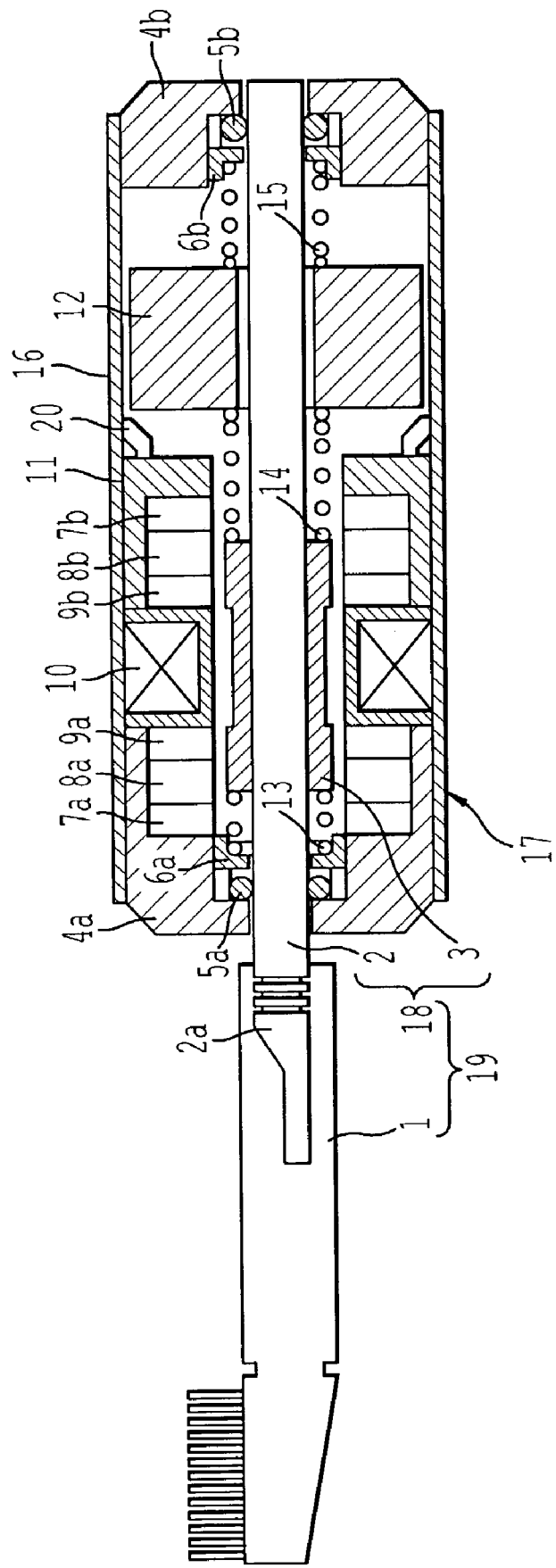
FIG. 1 is a cross-sectional view of an electric toothbrush according to an embodiment of the present invention.

The embodiments will now be described with reference to the accompanying drawings, wherein like reference numerals designate corresponding or identical elements throughout the various drawings.

FIG. 1 is a cross-sectional view of an electric toothbrush according to an embodiment of the present invention. Referring to FIG. 1, an electric toothbrush includes a linear oscillator 17. The linear oscillator 17 includes a shield case 16, a plunger 3 and a drive shaft 2 provided in the shield case 16 to be linearly movable. The drive shaft 2 is interference fitted into the plunger 3. The drive shaft 2 and the plunger 3 form a movable part 18. The plunger 3 is a formed in a substantially cylindrical shape and made of magnetic material. First and second bearing supports (4a and 4b) are mounted at the both ends of the shield case 16 in the shaft direction. Each of the bearing supports (4a and 4b) receives each end of the drive shaft 2 via each bearings (5a and 5b) which is provided in the bearing supports (4a and 4b). Accordingly, the drive shaft 2 is linearly movable with respect to the shield case 16. On the drive shaft 2, a vibration-absorber 12 is mounted in the axis direction with a distance from the plunger 3 so that the vibration-absorber 12 slides freely along the drive shaft 2. One shaft end (2a) of the drive shaft 2 protrudes from the first bearing support (4a). A brush part 1 is detachably attached to the one shaft end (2a). A driving part 19 includes the movable part 18 and the brush part 1. The driving part 19 and the vibration-absorber 12 are independently movable.

A ring-shaped coil 10 is fixed around the outer circumference of the plunger 3 within the shield case 16. The coil 10 is provided between ring-shaped permanent magnets (8a and 8b). The permanent magnets (8a and 8b) are magnetized symmetrically with respect to the coil 10. Second yoke (9a) is provided between the coil 10 and the permanent magnet (8a). Similarly, second yoke (9b) is provided between the coil 10 and the permanent magnet (8b). First yoke (7a) is provided to sandwich the permanent magnet (8a) between the first yoke (7a) and the second yoke (9a). Similarly, first yoke (7b) is provided to sandwich the permanent magnet (8b) between the first yoke (7b) and the second yoke (9b).

The first yoke (7b), the permanent magnet (8b) and the second yoke (9b), which are located at the vibration-absorber 12 side with respect to the coil 10, are held at the specific position each with the yoke pedestal 11 mounted in the inner surface of the shield case 16.

A first spring support (6a) is provided in the first bearing support (4a). A first spring 13 is provided between the first spring support (6a) and the plunger 3. A second spring 14 is provided between the plunger 3 and the vibration-absorber 12. A second spring support (6b) is provided in the second bearing support (4b). A third spring 15 is provided between the second spring support (6b) and the vibration-absorber 12. The first spring 13, the second spring 14, and the third spring 15 provide pressing force along the axial direction of the drive shaft 2.

When electric current is not supplied to the coil 10, the plunger 3 or the drive part 19 is in the static status at a position where the pressing force by the first, second and third springs (13, 14, and 15) and a magnetic force applied to the plunger 3 by the permanent magnets (8a and 8b) via the first yokes(7a and 7b) and the second yokes (9a and 9b) are balanced. When electric current having one direction is supplied to the coil 10, the magnetic flux of, for example, the first permanent magnet (8a) is weakened. Accordingly, the drive part 19 moves to the second permanent magnet (8b). When electric current having an opposite direction is supplied to the coil 10, the magnetic flux of the second permanent magnet (8b) is weakened. Accordingly, the drive part 19 moves to the first permanent magnet (8a). Thus, by supplying alternate current to the coil 10, the drive part 19 reciprocally moves along the axis direction of the drive shaft 2.

The reciprocal movement of the drive part 19 and the vibration-absorber 12 may be regarded as a vibration model of two particle system. By reciprocally vibrating the drive part 19 with a natural frequency, the drive part 19 and the vibration-absorber 12 reciprocally vibrate in the same phase (a first mode), or the drive part 19 and vibration-absorber 12 reciprocally vibrate in the opposite phases, respectively (a second mode). Namely, the drive part 19 and the vibration-absorber 12 resonate in the first or second mode. Therefore, the secure and quick brushing may be carried out.

In the linear oscillator 17 according to the present embodiment of the present invention, the yoke stand 11 is provided such that the rear end of the yoke stand 11 is positioned at the let side of the space in which the vibration-absorber 12 vibrates in FIG. 1. A projection 20 is formed by pressing a portion of the shield case 16 inwardly. The projection 20 engages with the rear end of the yoke stand 11. Accordingly, the space in which the vibration-absorber 12 vibrates in the shield case 16 increases in a radial direction. Thus, the size of the vibration-absorber 12 may be increased to increase the weight of the vibration-absorber 12. In order to increase the space in which the vibration-absorber 12 vibrates, the length of the shield case 16 along the axial direction may be increased.

The vibration-absorber 12 is made of, for example, iron, copper and brass. In order to increase the weight of the vibration-absorber 12, a material having a higher specific gravity may be employed. The weight of the drive part 19 is the sum of weight of the brush part 1 and the movable part 18. Namely, it is the sum of the weight of the brush part 1, the drive shaft 2 and the plunger 3.

Figure 2:
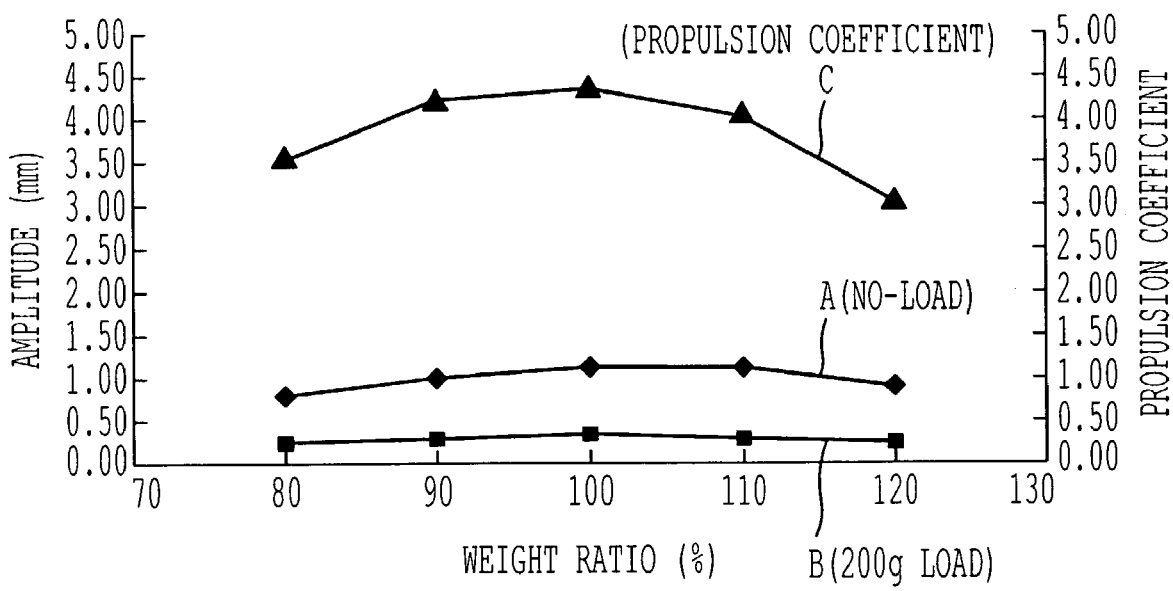
FIG. 2 is a graph showing a relationship between the weight ratio and an amplitude.
Figure 3:
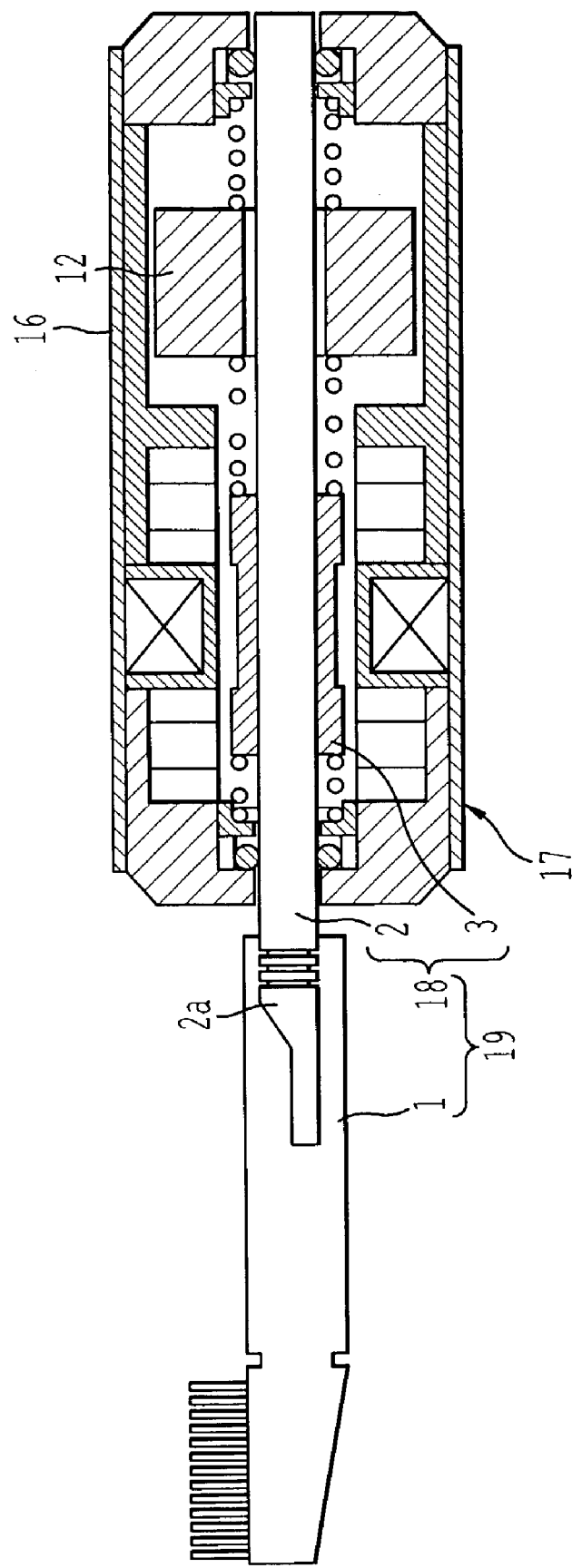
FIG. 3 is a cross-sectional view of an electric toothbrush of a background art.

Referring to FIG. 2, the line A shows a no-load condition and the line B shows a 200 g load condition. Referring to FIG. 2 and Table 1, the amplitude has a maximum value when the weight ratio is 100%. The weight ratio is a ratio of the weight (Wa) of the vibration-absorber 12 to the weight (m) of the drive part 19 (Wa/m). Namely, the amplitude has a maximum value when the weight of the vibration-absorber 12 (Wa) is equal to the weight (m) of the drive part 19.

In addition, vibration characteristic is correlated with propulsion of the linear oscillator 17. Referring to FIG. 2 and Table 1, the propulsion coefficient (C) has a maximum value when the weight ratio is 100%. The propulsion coefficient (C) is calculated according to the following formula:

$$C = mr(2\pi f)^2$$

m: the weight of the drive part
r: the amplitude of vibratio
f: frequency

TABLE 1

| Weight Ratio (%) | No-load Amplitude (mm) | 200 g Load Amplitude (mm) | Propulsion Coefficient |
|---|---|---|---|
| 80 | 0.80 | 0.23 | 3.56 |
| 90 | 1.00 | 0.28 | 4.24 |
| 100 | 1.12 | 0.33 | 4.38 |
| 110 | 1.11 | 0.27 | 4.05 |
| 120 | 0.90 | 0.23 | 3.06 |

In the present embodiment, the weight of the vibration-absorber 12 (Wa) is substantially equal to the weight (m) of the drive part 19. Accordingly, the propulsion coefficient (C) has a maximum value. Although it is necessary to increase the space in which the vibration-absorber 12 vibrates in the shield case 16, the size of the magnetic circuit for providing a suitable amplitude to the drive part 19 may reduce more. As a result, the size of the linear oscillator 17 or the size of the electric toothbrush may be reduced.

In order to obtain powerful teeth polishing feeling, the amplitude under the 200 g load condition is within 0.30 mm±10%. Referring to FIG. 2 and Table 1, the amplitude under the 200 g load condition is within 0.30 mm±10% when the weight ratio is at least 90% and at most 100%.

According to the present embodiment, the size of the electric toothbrush as well as the number of parts may be reduced. Further, even when the brush part is replaced with several kinds of brushes having different weights, the powerful feeling of the teeth polishing remains unchanged as long as weight ratio is at least 90% and at most 100%.

Obviously, numerous modifications and variations of the present invention are possible in the light of the above teachings. It is therefore to be understood that within the scope of the appended claims, the invention may be practiced otherwise than as specifically described herein.

What is claimed as new and desired to be secured by Letters Patent of the United States is:

1. An electric toothbrush comprising;
   a drive part comprising;
      a drive shaft provided to be lineally movable; and
      a brush part detachably attached to one end of the drive shaft;
   a driver configured to apply reciprocal force to the drive shaft to reciprocally lineally move the drive shaft;
   a vibration-absorber connected to the drive shaft via a spring to be lineally movable along the drive shaft; and
   an outer case housing the drive shaft, the driver, and the vibration-absorber,
   wherein the vibration-absorber is provided within an open area that extends from the drive shaft to an inner surface of the outer case.

2. An electric toothbrush according to claim 1, wherein the driver comprises;
   a plunger fixed to the drive shaft;
   first and second permanent magnets provided to provide magnetic power to the plunger; and
   a coil provided between the first and second permanent magnets and facing the plunger.

3. An electric toothbrush according to claim 1, wherein the electric toothbrush comprises;
   first and second bearing supports to support the drive shaft;

a second spring provided between the first bearing support and the drive shaft; and a third spring provided between the vibration-absorber and the second bearing support.

4. An electric toothbrush according to claim 1, wherein the outer case includes at least one projection projected inwardly to hold the driver.

5. An electric toothbrush according to claim 1, wherein a weight ratio of a weight of the vibration-absorber to a weight of the drive part is at least 0.9 and at most 1.1.

6. An electric toothbrush according to claim 5, wherein the weight ratio is substantially equal to 1.0.

7. A brushing device, comprising;
a brush part;
a movable part including a drive shaft provided to be lineally movable;
a driver configured to apply reciprocal force to the drive shaft to reciprocally lineally move the drive shaft;
a vibration-absorber connected to the drive shaft via a spring to be lineally movable along the drive shaft; and
an outer case housing the drive shaft, the driver, and the vibration-absorber,
wherein the vibration-absorber is provided within an open area that extends from the drive shaft to an inner surface of the outer case.

8. A brushing device according to claim 7, wherein the driver comprises;
a plunger fixed to the drive shaft;
first and second permanent magnets provided to provide magnetic power to the plunger; and
a coil provided between the first and second permanent magnets and facing the plunger.

9. A brushing device according to claim 7, further comprising;
first and second bearing supports to support the drive shaft;
a second spring provided between the first bearing support and the drive shaft; and
a third spring provided between the vibration-absorber and the second bearing support.

10. A brushing device according to claim 7, wherein the outer case includes at least one projection projected inwardly to hold the driver.

11. A brushing device according to claim 7, wherein a weight ratio of a weight of the vibration-absorber to a sum of a weight of the movable part and a weight of the brush part attached to one end of the drive shaft is at least 0.9 and at most 1.1.

12. A brushing device according to claim 11, wherein the weight ratio is substantially equal to 1.0.

13. A brushing apparatus comprising;
a brush part;
a movable part including a drive shaft provided to be lineally movable;
driver means for applying reciprocal force to the drive shaft to reciprocally lineally move the drive shaft;
a vibration-absorber connected to the drive shaft via a spring to be lineally movable along the drive shaft; and
an outer case housing the drive shaft, the driver means, and the vibration-absorber,
wherein the vibration-absorber is provided within an open area that extends from the drive shaft to an inner surface of the outer case.

14. A brushing apparatus according to claim 13, wherein a weight ratio of a weight of the vibration-absorber to a sum of a weight of the movable part and a weight of the brush part attached to one end of the drive shaft is at least 0.9 and at most 1.1.

15. An electric toothbrush comprising;
a drive part comprising;
a drive shaft provided to be lineally movable; and
a brush part detachably attached to one end of the drive shaft;
a driver configured to apply reciprocal force to the drive shaft to reciprocally lineally move the drive shaft;
a vibration-absorber connected to the drive shaft via a spring to be lineally movable along the drive shaft;
a pedestal configured to hold at least a portion of the driver;
a bearing configured to support an end of the drive shaft; and
a projection engaged with the pedestal to provide an open space between the pedestal and the bearing within which the vibration-absorber is provided.

16. An electric toothbrush according to claim 15, further comprising a case in which the drive shaft, pedestal, and vibration-absorber are housed, wherein the open space extends from the drive shaft to an inner surface of the case.

17. An electric toothbrush according to claim 15, wherein a weight ratio of a weight of the vibration-absorber to a weight of the drive part is at least 0.9 and at most 1.1.

18. A brushing device comprising;
a brush part;
a movable part including a drive shaft provided to be lineally movable;
a driver configured to apply reciprocal force to the drive shaft to reciprocally lineally move the drive shaft;
a vibration-absorber connected to the drive shaft via a spring to be lineally movable along the drive shaft;
a pedestal configured to hold at least a portion of the driver;
a bearing configured to support an end of the drive shaft; and
a projection engaged with the pedestal to provide an open space between the pedestal and the bearing within which the vibration-absorber is provided.

19. A brushing device according to claim 18, further comprising a case in which the drive shaft, pedestal, and vibration-absorber are housed, wherein the open space extends from the drive shaft to an inner surface of the case.

20. A brushing device according to claim 18, wherein a weight ratio of a weight of the vibration-absorber to a sum of a weight of the movable part and a weight of the brush part attached to one end of the drive shaft is at least 0.9 and at most 1.1.

21. A brushing apparatus comprising;
a brush part;
a movable part including a drive shaft provided to be lineally movable;
driver means for applying reciprocal force to the drive shaft to reciprocally lineally move the drive shaft;
a vibration-absorber connected to the drive shaft via a spring to be lineally movable along the drive shaft, a pedestal configured to hold at least a portion of the driver means;
a bearing configured to support an end of the drive shaft; and
a projection engaged with the pedestal to provide an open space between the pedestal and the bearing within which the vibration-absorber is provided.

22. A brushing apparatus according to claim 21, further comprising a case in which the drive shaft, pedestal, and vibration-absorber are housed, wherein the open space extends from the drive shaft to an inner surface of the case.

23. A brushing apparatus according to claim 21, wherein a weight ratio of a weight of the vibration-absorber to a sum of a weight of the movable part and a weight of the brush part attached to one end of the drive shaft is at least 0.9 and at most 1.1.

24. A brushing apparatus comprising;
a brush unit attached to an end of a drive shaft;
a driving unit configured to move the drive shaft;
a vibration-absorbing unit configured to absorb vibrations caused by the movement of the drive shaft;
a pedestal configured to hold at least a portion of the driving unit;
a bearing configured to support an end of the drive shaft; and
a projection engaged with the pedestal to provide an open space between the pedestal and the bearing within which the vibration-absorbing unit is provided.

25. A brushing apparatus according to claim 24, further comprising a case in which the drive shaft, pedestal, and vibration-absorbing unit are housed, wherein the open space extends from the drive shaft to an inner surface of the case.

26. A brushing apparatus according to claim 24, wherein a ratio of a weight of the vibration-absorbing unit to a sum of a weight of the brush and driving units is from 0.9 to 1.1.

27. A brushing apparatus comprising:
a brush unit attached to an end of a drive shaft;
a driving unit configured to move the drive shaft;
a vibration-absorbing unit configured to absorb vibrations caused by the movement of the drive shaft; and
an outer case housing the drive shaft, the driving unit, and the vibration-absorbing unit,
wherein the vibration-absorbing unit is provided within an open area that extends from the drive shaft to an inner surface of the outer case, and
wherein a ratio of a weight of the vibration-absorbing unit to a sum of a weight of the brush and driving units is from 0.9 to 1.1.

* * * * *

UNITED STATES PATENT AND TRADEMARK OFFICE
CERTIFICATE OF CORRECTION

PATENT NO.        : 7,328,474 B2
APPLICATION NO. : 10/340632
DATED             : February 12, 2008
INVENTOR(S)       : Takahiro Nishinaka et al.

It is certified that error appears in the above-identified patent and that said Letters Patent is hereby corrected as shown below:

Title page, Item (75), line 4, change "Shiga" to --Higashiasai-gun--; and

Column 4, line 2, change "vibratio" to --vibration--.

Signed and Sealed this

Sixteenth Day of September, 2008

JON W. DUDAS
*Director of the United States Patent and Trademark Office*